United States Patent
Al-Qaoud et al.

(10) Patent No.: US 10,278,404 B2
(45) Date of Patent: May 7, 2019

(54) IMMUNIZED CAMEL MILK-BASED COMPOSITION FOR THE TREATMENT OR PREVENTION OF GASTROINTESTINAL INFECTIONS

(75) Inventors: Khaled Mahmood Al-Qaoud, Amman (JO); Penelope Agmad Shihab, Amman (JO); Luay Fawzi Abu-Oatousch, Amman (JO); Christopher R. Lowe, Cambridge (GB)

(73) Assignee: AL-URDONIA LEMUDADDAT AL-AJSAM CO, Amman (JO)

( * ) Notice: Subject to any disclaimer, the term of this patent is extended or adjusted under 35 U.S.C. 154(b) by 496 days.

(21) Appl. No.: 13/609,350

(22) Filed: Sep. 11, 2012

(65) Prior Publication Data

US 2014/0072649 A1  Mar. 13, 2014

(51) Int. Cl.
*A61K 35/20* (2006.01)
*A23C 9/20* (2006.01)
*A23C 9/158* (2006.01)

(52) U.S. Cl.
CPC .............. *A23C 9/20* (2013.01); *A23C 9/1585* (2013.01); *A61K 35/20* (2013.01); *A23C 2230/15* (2013.01); *Y02A 50/47* (2018.01); *Y02A 50/473* (2018.01); *Y02A 50/475* (2018.01); *Y02A 50/481* (2018.01)

(58) Field of Classification Search
CPC .................................................... A61K 35/20
USPC ......................................................... 424/535
See application file for complete search history.

(56) References Cited

U.S. PATENT DOCUMENTS

| 7,883,691 B2 * | 2/2011 | Kalejman | A61K 8/986 424/535 |
| 2007/0154443 A1 * | 7/2007 | Kalejman | 424/74 |
| 2011/0268743 A1 * | 11/2011 | Benyacoub et al. | 424/157.1 |

FOREIGN PATENT DOCUMENTS

| CN | 101045750 | * 10/2007 |
| WO | WO 2008/013455 | * 1/2008 |
| WO | WO 2011/104565 | * 9/2011 |

OTHER PUBLICATIONS

Madany, R.M. BioTechnology: An Indian Journal. 2009. vol. 3, No. 1, pp. 30-34.*
Shamsia, S.M. International Journal of Genetics and Molecular Biology. 2009. vol. 1, No. 2, pp. 52-58.*
Hurley et al. Nutrients. 2011. vol. 3, pp. 442-474.*
Odongo et al. Current Res. Nutr. Food Sci. 2016. vol. 4, No. 2, pshrd 80-89.*
Website document entitled "Camel milk and cheese making". First available online in 2002. 8-pages. Obtained from http://www.fao.org.*
Seifu, E. Livestock Research for Rural Development. 2007. vol. 19, No. 6, 8-pages.*
Wlodzimierz, Otto, et al., Randomized control trials using a tablet formulation of hyperimmune bovine colostrum to prevent diarrhea caused by enterotoxigenic *Esherichia coli* in volunteers, Scandanavian Journal of Gastroenterology, 2011; 46: 862-868.
Mehra, Raj, et al., Milk immunoglobulins, International Dairy Journal 16 (2006) 1262-1271.
Cao, Wei, et al., ISpecitic igG activity against diarrheagenic bacteria in bovine immune milk and effect of pH on its antigen-binding activity upon heat, Journal of Dairy, 2010 77, 220-224.
Husu, J., et al., Production of hyperimmune bovine colostrum against Campylobacter jejuni, Journal of Applied Bacteriology, 1993 74, 564-569.
Shabo, Yosef, et al., Camel Milk for Food Allergies in Children, Immunology and Allergies. 2005 7, 796-798.
Unknown Author, website: www.kamelka.nl/kamelka-bonbons-made-entirely-from-camel-milk/.
Gustafsson, Anki, et al., Carbohydrate phenotyping of human and animal milk glycoproteins, Glycoconjugate Journal, 2005 22, 109-118.
Hurley, Walter L., et al., Perspectives on Immunoglobulins in Colostrum and Milk, Nutrients, 2011 3, 442-474.
Office Action from related United Kingdom Application No. GB 1316120.3, dated Sep. 11, 2014, 3 pgs.
Office Action from related United Kingdom Application No. GB 1316120.3, dated May 9, 2017, 2 pgs.

* cited by examiner

*Primary Examiner* — Christopher R Tate
(74) *Attorney, Agent, or Firm* — The Law Firm of Brett M. Maland; Brett M. Maland (57) ABSTRACT

The present invention relates to a novel composition with milk of immunized camelid, particularly, (*Camelus dromedarius*) as the main component (i.e. active ingredient) and a method for the treatment or prevention of gastrointestinal infections, particularly, infections caused by *Escherichia coli* (*E. coli*), *Helicobacter Pylori* (*H. pylori*), *Campylobacter jejuni* (*C. jejuni*), *Salmonella enterica*, *Shigella dysenteriae*, *Clostridium perfringens*, or *Yersinia enterocolitica*. Said composition is prepared in the form of pharmaceutical, nutraceutical, or health food preparations. The present invention also discloses a process of preparing said composition.

10 Claims, 7 Drawing Sheets

IMMUNIZED CAMEL MILK-BASED COMPOSITION FOR THE TREATMENT OR PREVENTION OF GASTROINTESTINAL INFECTIONS

FIELD OF THE INVENTION

The field of this invention relates to a composition for the treatment or prevention of gastrointestinal infections, and more particularly, the invention relates to a composition based on immunized camelid milk, particularly *Camelus dromedarius* as the active ingredient, and a process of preparing the composition.

BACKGROUND OF THE INVENTION

Gastrointestinal infections are considered a major health problem for many people. The resulting diseases of these infections can be life threatening. Gastrointestinal infections are often caused by a wide range of microorganisms, for example *Escherichia coli* (*E. coli*), *Helicobacter Pylori* (*H. pylori*), *Campylobacter jejuni* (*C. jejuni*), and many other microorganisms. These microorganisms are responsible for many diseases, among which gastroenteritis, enteritis, gastritis, peptic ulcer, and duodenal ulcer.

Animal milk has been used in the preparation of pharmaceutical and nutraceutical compositions. Milk of ruminants, and predominantly bovine milk, has been utilized most. Among drawbacks of cow milk is a wide-spread allergy to it, affecting in several of its forms as much as 50% individuals in some populations. It is an object of this invention to provide a composition comprising immunized milk which keeps all the benign properties of milk but is free of the drawbacks related to cow milk. Camel milk has been traditionally used by certain ethnic groups, and it was found that, in some respects, its composition is closer to the human milk than cow milk.

Passive immunity is provided to newborns by Immunoglobulins present in colostrum until its own immune system matures. The concentration in colostrum of specific antibodies against pathogens can be raised by immunizing a mammal with these pathogens or their antigens. Immunized milk products are preparations made of such hyper-immune colostrum or antibodies enriched from it. These preparations can be used to give effective specific protection against different diseases. Colostral immunoglobulin supplements designed for farm animals are commercially available in many countries. Also, some immunized milk products that contain specific antibodies against certain pathogens have been launched in the market. A number of clinical studies are currently in progress to evaluate the efficacy of immunized milks in the prevention and treatment of various human infections, including those caused by antibiotic resistant bacteria. Immunized milk products are examples of health-promoting functional foods, or nutraceuticals.

SUMMARY OF THE INVENTION

It is an object of the present invention to eliminate the disadvantages of the prior art by providing a composition comprising treated immunized camelid milk in a pharmaceutically acceptable vehicle for the treatment or prevention of gastrointestinal infections, especially infections caused by *Escherichia* (*E. coli*), *Helicobacter Pylori* (*H. pylori*), *Campylobacter jejuni* (*C. jejuni*), *Salmonella enterica* (*S. enterica*), *Shigella dysenteriae* (*S. dysentriae*), *Clostridium perfringens* (*C. perfringens*), or *Yersinia enterocolitica* (*Y. enterocolitica*).

A second object of the present invention, is to provide a process of preparing the composition comprising;
  a. immunizing a female camelid with a vaccine of *Escherichia coli* (*E. coli*), *Helicobacter Pylori* (*H. pylori*), *Campylobacter jejuni* (*C. jejuni*), *Salmonella enterica* (*S. enterica*), *Shigella dysenteriae* (*S. dysentriae*), *Clostridium perfringens* (*C. perfringens*), or *Yersinia enterocolitica* (*Y. enterocolitica*);
  b. Obtaining milk from the camelid;
  c. Treating the milk at a temperature of 0° C. for 1-2 hours and centrifuging at 15000 rpm to remove lipids;
  d. Treating the milk with rennin or acetic acid to reduce protein content;
  e. Pasteurizing the milk at a temperature ranging from 65° C. to 72° C. for 15 minutes; and
  f. Preparing the milk in an acceptable carrier to be used for gastrointestinal infections.

Another object of the present invention, is to provide a method for the treatment or prevention of gastrointestinal infections, comprising administering to an infected human an effective amount of the composition of invention.

Preferably, the camelid described in the invention is chosen from the genus *Camelus, Llama*, or *Vicuna*. More preferably, the camelid is Camelus dromedaries.

The camelid described in the invention is immunized with gastrointestinal pathogen, preferably *Escherichia coli* (*E. Coli*), *Helicobacter Pylori* (*H. pylori*), *Campylobacter jejuni* (*C. jejuni*), *Salmonella enterica* (*S. enterica*), *Shigella dysenteriae* (*S. dysentriae*), *Clostridium perfringens* (*C. perfringens*), or *Yersinia enterocolitica* (*Y. enterocolitica*).

Preferably, the composition of the invention is in the form of form of pharmaceutical, nutraceutical or health food preparation. As a further aspect of the invention, the composition is provided for use in a medicament for the treatment or prevention of gastrointestinal infections. The infections are caused by at least one of *Escherichia coil* (*E. coli*), *Helicobacter Pylori* (*H. pylori*), *Campylobacter jejuni* (*C. jejuni*), *Salmonella enterica* (*S. enterica*), *Shigella dysenteriae* (*S. dysentriae*) *Clostridium perfringens* (*C. perfringens*), or *Yersinia enterocolitica* (*Y. enterocolitica*).

DETAILED DESCRIPTION OF THE INVENTION

The composition of this invention comprises immunized camelid milk as the active ingredient in an acceptable carrier.

The composition is used for the treatment or prevention of an infection caused by gastrointestinal pathogens or a disease associated with infection by a gastrointestinal pathogen in mammals. The gastrointestinal pathogens could be for example Escherichia Coli (E. coli), Helicobacter Pylori (H. pylori), Campylobacter jejuni (C. jejuni), Salmonella enterica (S. enterica), Shigella dysenteriae (S. dysentriae), Clostridium perfingens (C. perfringens), or Yersinia enterocolitica (Y. enterocolitica).

The camelid, preferably Arabian camel (Camelus dromadarius), is immunized subcutaneously with an initial dose of 3 ml of prepared vaccine from a pathogen. The vaccinated camel is boosted 4 times at 2 week intervals with 5 ml of vaccine for each booster.

The vaccine is prepared from Escherichia coli (E. coli), Helicobacter Pylori (H. pylori), Campylobacter jejuni (C. jejuni), Salmonella enterica (S. enterica), Shigella dysenteriae (S. dysentriae), Clostridium perfringens (C. perfringens), or Yersinia enterocolitica (Y. enterocolitica), as shown in the Examples.

The composition, according to the present invention, is intended for treating gastrointestinal infections orally in an acceptable carrier. This carrier is in the form of pharmaceutical, nutraceutical, or food preparation. The composition can be in the form of liquid or solid suitable for oral administration, preferably in the form which include, but is not limited to oral solutions, oral suspensions, oral emulsions, tablets, and powders. The composition may include preservatives, ionic and non ionic buffered agents and additives commonly used in the preparation of oral compositions. For liquid oral compositions such as solutions, suspensions or emulsions, the solvent is preferably water or a multiple-component aqueous solution compatible with the oral use. The components of the composition and their ratios could be adjusted according to the acceptable carrier and the intended application of the composition.

In addition, the composition can be in the form which include, but is not limited to beverage, dairy product, food, food additive, food coating, processed food or beverage, or dried material or dried food supplement.

The present invention further relates to a process for the preparation of the composition, comprising:
1. Immunizing a female camelid with a vaccine of Escherichia coli Escherichia coli (E. coli), Helicobacter Pylori (H. pylori), Campylobacter jejuni (C. jejuni), Salmonella enterica (S. enterica), Shigella dysenteriae (S. dysentriae), Clostridium perfringens (C. perfringens), or Yersinia enterocolitica (Y. enterocolitica);
2. Obtaining milk from the female camelid;
3. treating the camelid milk at a temperature of 0° C. for 1-2 hours and centrifuging at 15000 rpm to remove lipids;
4. Treating the milk with rennin or acetic acid to reduce protein content;
5. Pasteurizing the camelid milk, at a temperature ranging from 65° C. to 72° C. for 15 minutes; and
6. Preparing the camelid milk in an acceptable carrier to be used for gastrointestinal infections.

The invention will be further described and illustrated in the following examples.

EXAMPLES

The following examples illustrate the present invention without, however, limiting the same thereto.
For Escherichia coli (E. coli)
Antigen Preparation for Immunization

Example 1

Whole Cell E. coli Vaccine Preparation

Bacteria were cultured in nutrient broth and whole cell antigens were fixed overnight in 0.6% Formalin-PBS (Phosphate Buffered Saline) and re-suspended in sterile 0.015M NaCl after washing. The formalin fixed cell suspension was adjusted to 2 McFarland and used for 1st immunization dose.

Example 2

Outer Membrane Antigen Preparation of E. coli O157:H7

E. coli cell pellet was re-suspended into 2 mL of PBS then sonicated for 20 minutes (Sweep program) using Sono-Cleansonicator. The mixture was centrifuged for 20 min at 13,400 rpm at (Room Temperature) R.T. and the sonication step was repeated for two more times. After centrifugation, the supernatant fluid was concentrated using Vivaspin column (M.wt 30 kD). Protein content was determined using Bradford protein assay. 0.5 mg protein was mixed with similar volume of incomplete fruend's adjuvant and was used to boost the camels.

Example 3

Camel Immunization

For each infection model two adult female Arabian camels (Camelus dromedarius) were used; one as control and the other was immunized subcutaneously with an initial dose of 3 ml of prepared Escherichia coli vaccine. The vaccinated camel was boosted 4 times at 2 week intervals with 5 ml of vaccine for each booster. The camels were kept in a farm for two months and under similar conditions.

Example 4

Milk Collection and Preparation

The milk was collected from each camel immediately before each immunization and at weakly intervals. The casein was precipitated from the pooled skimmed milk samples based on the technique of Brussow et al, (1987) by milk renneting with commercially available rennin (Valiren, USA) to obtain good curd contraction. The coagulated milk was heated to 56° C. for 10 minutes. Casein separation from lactoserum was carried out by filtration. For final clarification, the lactoserum was again centrifuged at 10,000 rpm for 30 min at 0° C. (Europa 24, Germany). The pellet was discarded and the supernatant was filtered using a millipore filter (0.4 μm), then 50 ml of filtered supernatant were lyophilized using Edward, EF Modulyolyophilizer (Britain) to reach a final volume of 20 ml which was used in experiment 1. For experiment 2 further lyophilizations were done by reducing the volume from 100 ml to 13 ml.

Example 5

Detection of Specific Antibodies Against E. Coli O157:H7 in Milk by Enzyme Linked Immunosorbent Assay (ELISA)

For milk antibody screening, the ELISA was performed. Flat bottomed 96 well polystyrene microtiter plates (Greiner, Germany) were coated with 100 µl of 10 µg/ml E. coli O157:1-17 antigens in carbonate-bicarbonate buffer (pH 9.6) overnight at 4° C. The plates were washed 3 times with 100 µl of 0.15 Molar (M) Phosphate Buffered Saline (PBS) (pH 7.2) containing 0.05% Tween 20 and blocked with 100 µl of 2% bovine serum albumin (BSA) in PBS for one hour at room temperature (RT). The Plates were washed again and 100 µl of serum samples diluted at 1:100 in 1% BSA were added in duplicates and incubated one hour at RT, whereas, the milk samples were added in duplicates without dilution Negative and positive control samples were incorporated in each plate. After washing, 100 µl of one of the horse radish peroxidase (HRP) conjugated protein A and protein G were diluted at 1:1000 in 1% BSA, and were added separately to each well. The Plates were incubated for one hour at RT and washed again. Finally, 100 µl of 0.1% O-phenylenediamine (Sigma, USA) containing hydrogen peroxide in 0.1 M citrate buffer (pH 4.5) were added to each well and absorbance was measured at 490 nm using ELISA reader (AsysHitech, Switzerland).

Example 6

Identification of Camel Milk Proteins Using Sodium Dodecyl Sulfate Polyacrylamide Gel Electrophoresis (SDS-PAGE)

Components of skimmed milk were fractionated by SDS-PAGE (after precipitation of casein). This was performed using Desaphor VE minigel (Heidelberg, Germany) in the discontinuous buffer system using 0.5 mm thick 10% acrylamide-bisacrylamide gels under non-reducing conditions as described by Hamers-Casterman at al. (1993). For preparing resolving gels; 4 mL distilled water, 2.5 mL running buffer (pH 8.8), 3.3 mL of 30% acrylamide-bisacrylamide solution, 100 µL of 10% ammonium persulfate (APS) and 10 µL Tetramethylethylenediamine (TEMED) were mixed. Stacking gels (4%) were prepared by adding 6 ml of distilled water, 2.5 ml staking buffer (pH 6.6), 1.3 mL of 30% acrylamide-bisacrylamide solution, 100 µl of 10% APS and 10 µl TEMED. The milk was mixed with an equal volume of sample buffer lacking B-mercaptoethanol (non-reducing conditions) (pH 6.8). For band size determination, molecular weight protein standard was used after being processed in a similar way as the milk samples. Electrophoresis was carried out using the running buffer with pH 8.3 at 120 volts for 60-120 minutes. The gel was stained with Coomassie brilliant blue R-250 (except if used for immunoblot) and destained by 20% acetic acid until clear bands were seen.

Example 7

In Vitro Activity of Camel Whey Against E. coli

Pour plate method was used to count the bacteria after incubation with camel whey according to the following protocol:
1. $1.5 \times 10^8$ E. coli CFU/ml (equivalent to 0.5 McFarland standard) were prepared;
2. 20 mg/ml total whey of Camel milk immunized and non-immunized with E. coli was prepared;
Equal volumes of Bacteria and whey (500 ul each) and incubate for 1 hr at 37 C and 9 ml of PBS was added to the mixture;
4. Using plate count method, serial dilutions of the mixture were plated on Mueller-Hinton (MH) Agar and incubated for 24 hr at 37 C,
5. The total count of bacteria (CFU/ml) was recorded for immunized and control whey preparation.

Example 8

In Vivo Activity of Camel Whey Against the Infection with E. coli O157:H7

Note: Animal model was approved by the ANIMAL CARE AND USE COMMITTEE (IACUC) at Jordan University for Science and Technology (JUST) and Philadelphia University (PU).

Infection Protocol:
1. 5 groups (6 animals each) of eight weeks old male BALB/c mice were used in this experiment;
2. Food was taken from the animal cages at the night before bacterial challenge;
3. Water bottles were removed from the cages 2 hours prior to infection of the mice;
4. 2 groups were infected with $10^{10}$ viable E. coli cells suspended in 100 µl 20% glucose-PBS and one group was given 20% glucose-PBS as negative control;
5. After 24 hours group 1 was treated orally using gavage with 300 ml whey of E. coli immunized camel whereas group 2 was treated with whey of non-immunized camel;
6. Feces were collected from mice of each group before infection and on daily intervals after infection. For each mouse, one feces piece was collected in 1.5 ml sterile tube containing 500 µl PBS. Feces solution was vortexed and then left to still down. 50 µl of the supernatant was inoculated and spread on MacConkey agar plate for E. coli O157:H7 bacteria identification;
7. After 7 days, the experiment was terminated by euthanized 3 randomly selected mice from each group by cervical dislocation. The cecum of each mouse was taken, digested, preserved in 5 ml PBS, vortexed, stilled down and then 50 µl of the supernatant was inoculated and spread on MacConkey agar plate for E. coli O157:H7 bacteria identification.

Example 9

In Vivo Activity of Camel Whey

Figure 1:
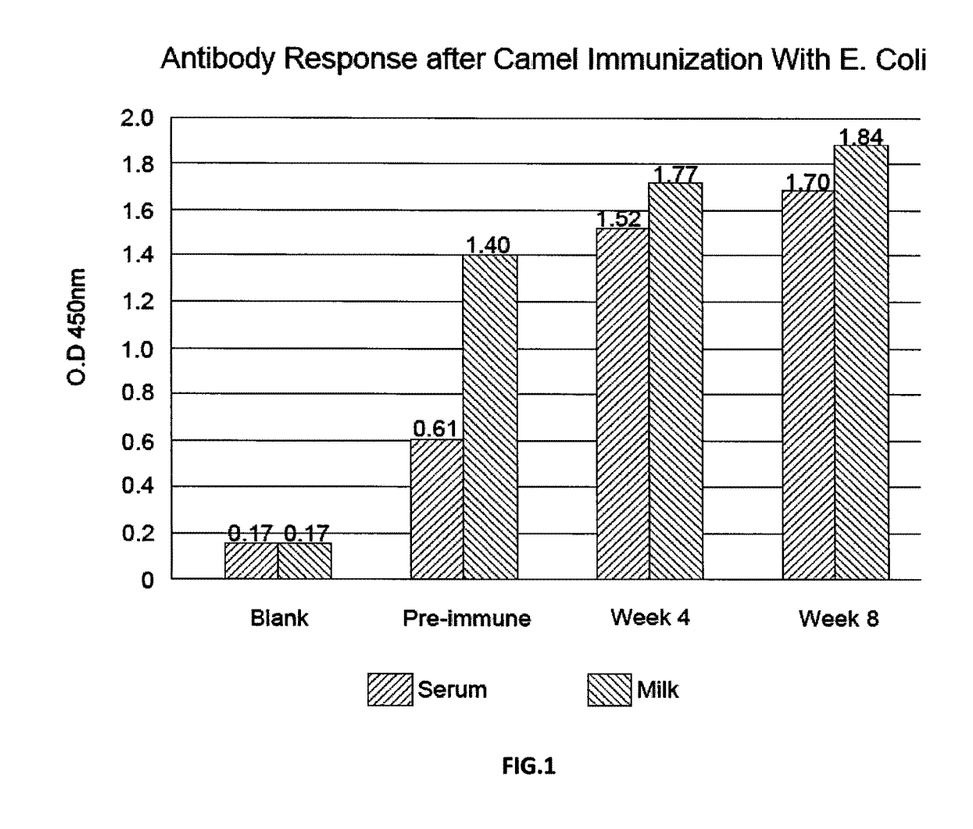
FIG. 1 shows antibody immune response in the serum and milk of camel immunized with *E. coli* over the period of immunization.
Figure 2:
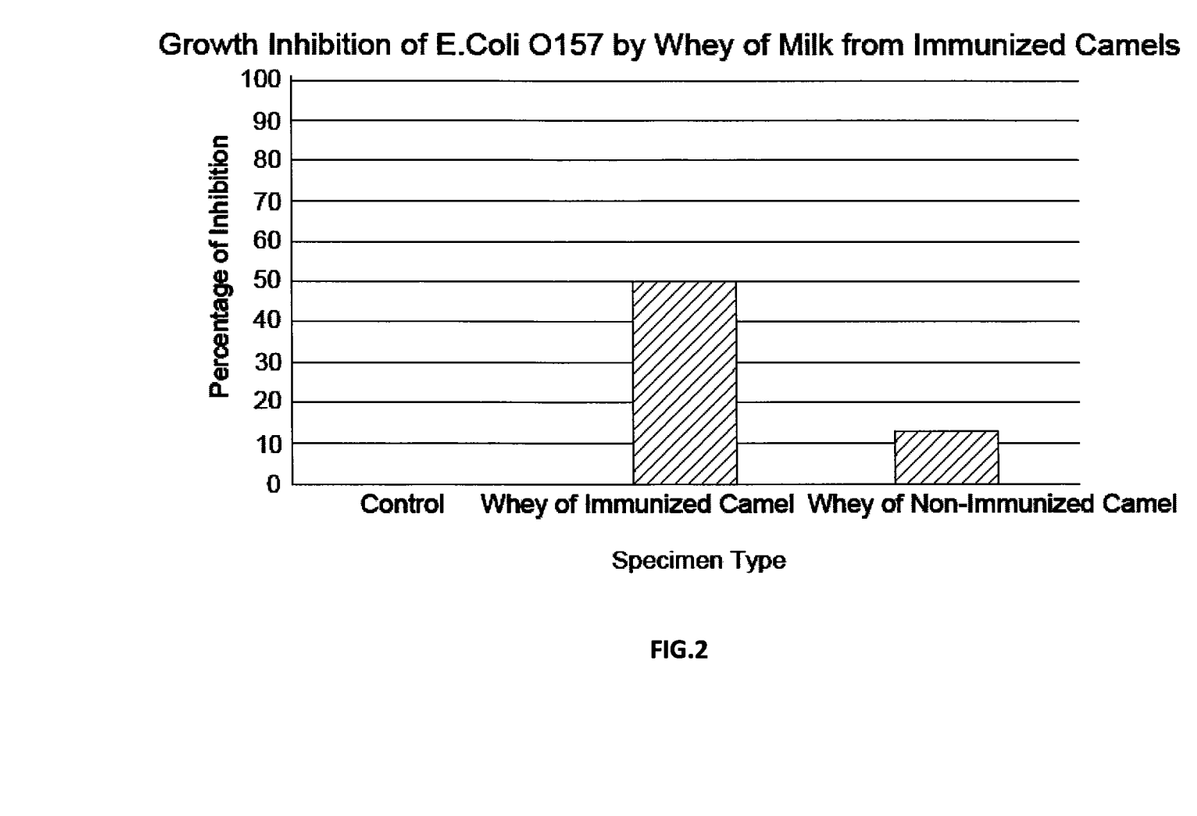
FIG. 2 shows growth inhibition of *E. coli* O157 by whey of milk from immunized camels.
Figure 3:
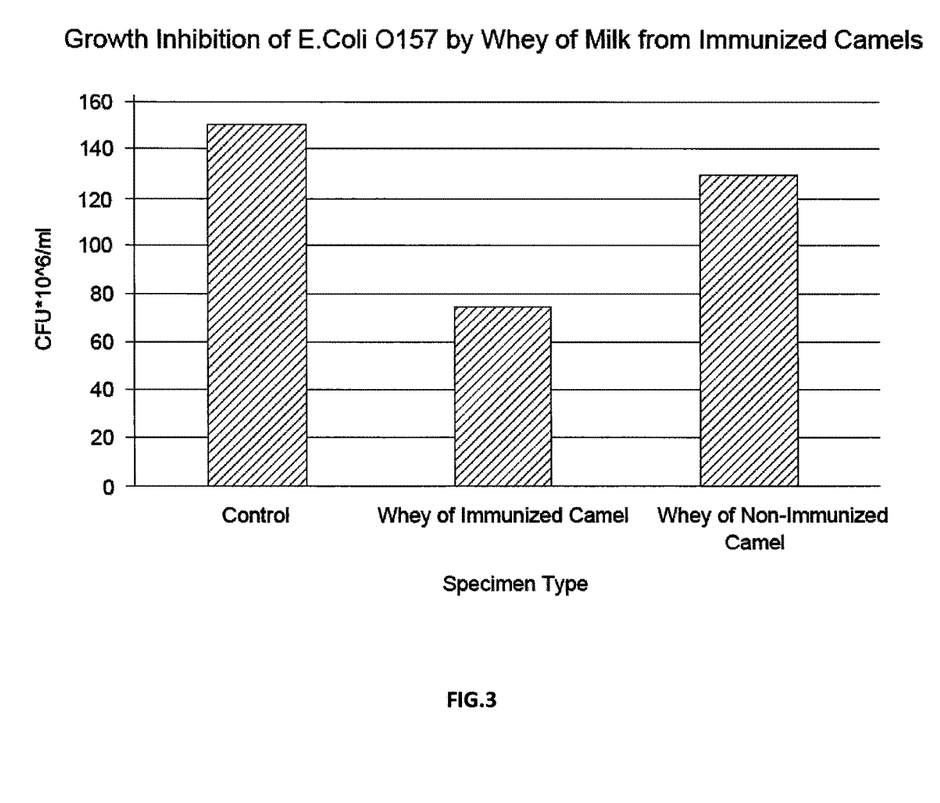
FIG. 3 shows growth inhibition of *E. coli* O157 by whey of milk from immunized camels.
Figure 4:
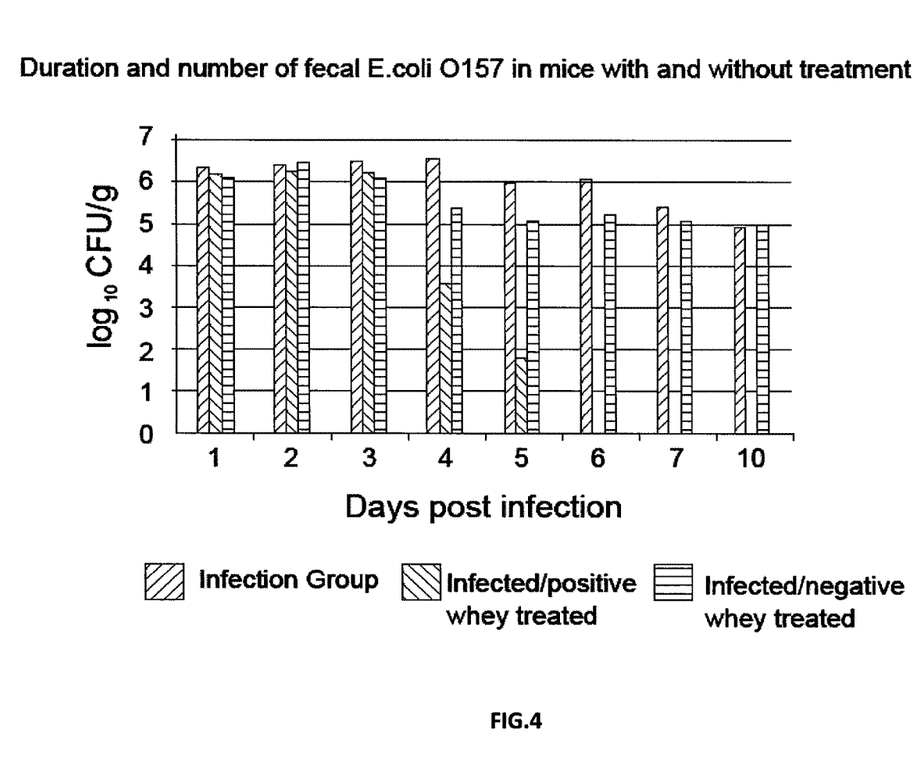
FIG. 4 shows the kinetic of *E. coli* eradication in mice infected with *E. coli* O157:H7 and treated with whey of milk from immunized and non-immunized camels.
Figure 5:
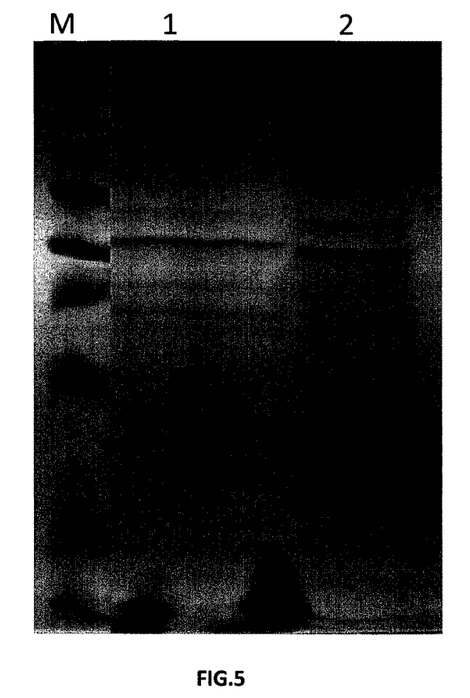
FIG. 5 shows SDS-PAGE of the outer membrane proteins (OMPs) extracted from *H. pylori* using 1% Tween 20 (1), or 1% Triton X-100 (2). M denotes protein molecular weight marker.

The bacterial clearance from the mice intestine was evaluated by culturing of the stool samples collected over the experimental period. FIG. 4 demonstrates clearly the treatment effect of whey of immunized camel in the eradication of E. coli. Both infected without treatment and infected, treated with negative whey did not reduce the bacterial load all over the experiment period (10 days). In contrast, by day 6, mice treated with whey of immunized camel were completely free E. coli.

For Helicobacter Pylori

Example 10

Extraction of H. Pylori Outer Membrane Proteins (OMPs)
1. 2 mL of autoclaved phosphate buffered saline (PBS, pH 7.2) was added to each agar plate, and then it was scraped using glass pasture pipette as scraper;
2. The cell suspension was pipette to 2 ml eppendorf tube, and then it was centrifuged at 8.000 rpm (microfuge) for 15 min at R.T;
3. The supernatant fluid was discarded and the cell pellet was re-suspended into 2 mL of PBS, washed once by centrifugation at 8,000 rpm for 15 min at R.T;

4. The pellet was re-suspended in 2 ml of 1% Tween 20 or 1% Triton X-100 in PBS;
5. After incubation for 5 min at R.T, the mixture was centrifuged for 20 min at 13,400 rpm at R.T;
6. The supernatant fluid (2 ml) was dialyzed overnight at 4 C against 2 L autoclaved PBS, and then concentrated by lyophilization.
7. The powder from each plate was dissolved in 200 µl autoclaved distilled water and then stored at 4 C;
8. SDS-PAGE and Urease test (using urea agar media plate) were done for the samples.

Example 11

Figure 6:
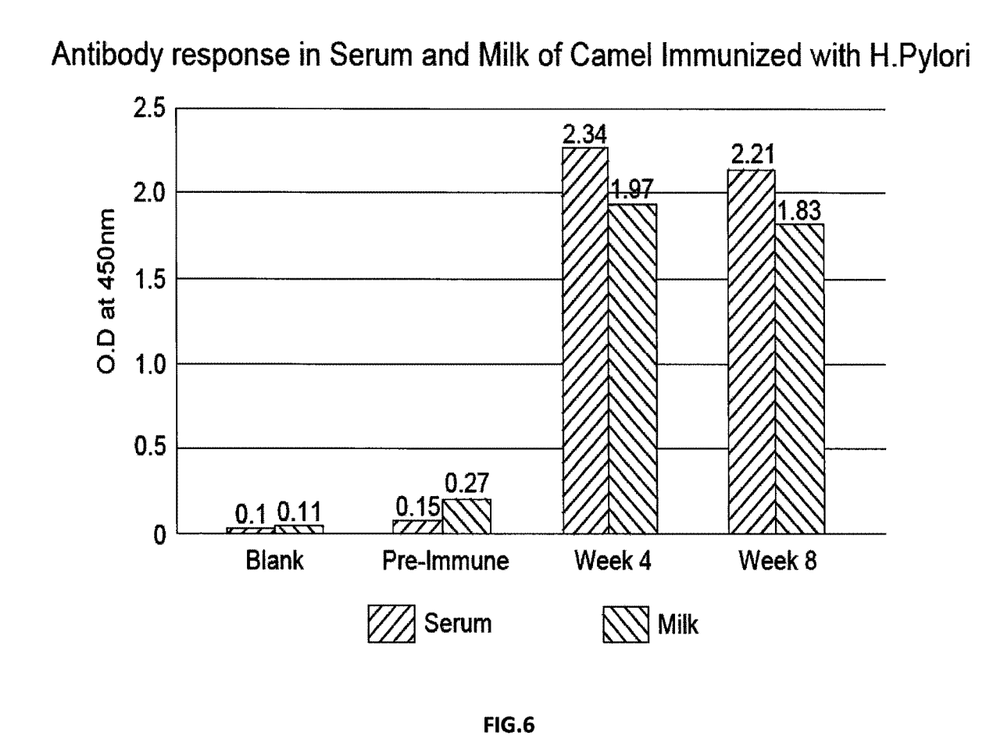
FIG. 6 shows antibody immune response in the serum and milk of camel immunized with *H. pylori* over the period of immunization.
Figure 7:
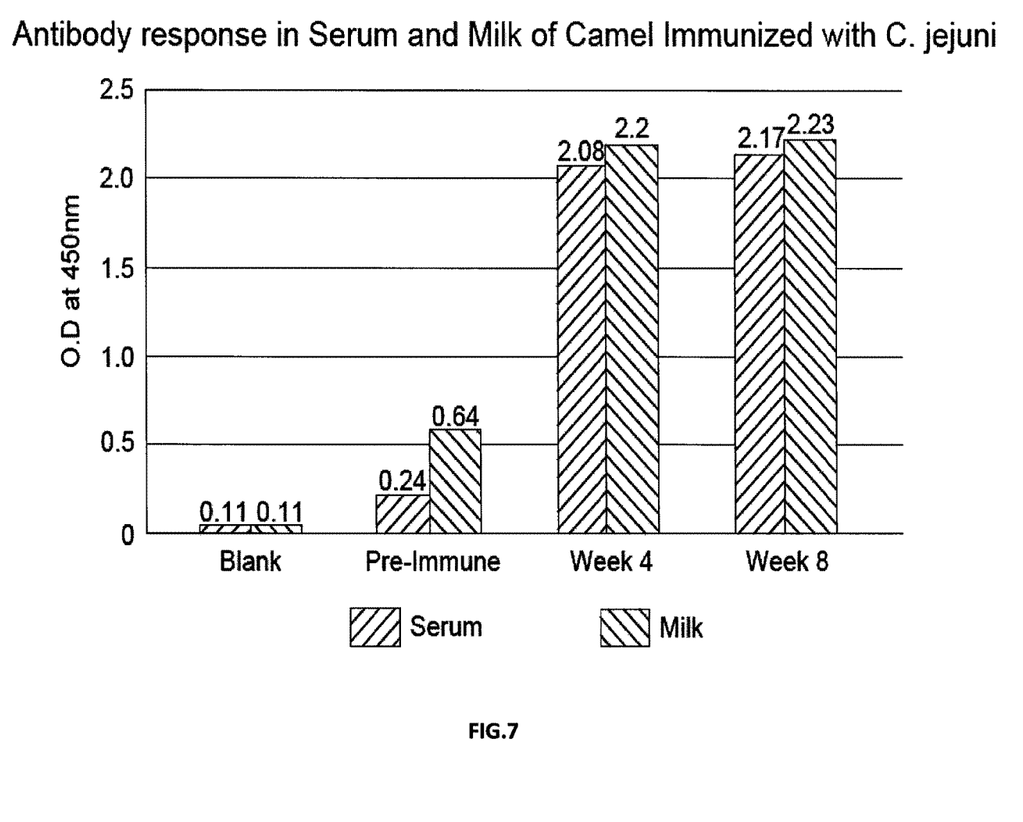
FIG. 7 shows antibody immune response in the serum and milk of camel immunized with *C. jejuni* over the period of immunization.

Immunization of Camel 8 years old female camel was immunized with OMP preparation in complete freunds adjuvant and boosted 5 times, 2 week intervals with OMP preparation in incomplete adjuvant. Antibody response in the serum and milk of immunized camels is shown in FIG. 6.

While the present invention has been described in details and with reference to specific embodiments thereof, it will be apparent to one skilled in the art that various additions, omissions and modifications can be made without departing from the spirit and scope thereof.

The invention claimed is:

1. A composition for the treatment or prevention of gastrointestinal infections caused by *Escherichia coli* (*E. coli*), *Helicobacter Pylori* (*H. pylori*) or *Campylobacter jejuni* (*C. jejuni*), comprising an effective amount of immunized Camelid milk, wherein said composition is prepared by the steps of:
    immunizing a Camelid with a gastrointestinal pathogen by artificially injecting said Camelid with said gastrointestinal pathogen, wherein said pathogen is *E. coli, H. pylori* or *C. jejuni*,
    treating the obtained milk with rennin or acetic acid under conditions suitable to reduce the protein content of the milk, and
    adding an acceptable oral carrier to the treated milk;
    wherein said composition is in the form of a pharmaceutical, nutraceutical or health food preparation.

2. The composition of claim 1, wherein said Camelid is from the genus *Camelia, Liam* or *Vicuna*.

3. The composition of claim 2, wherein said Camelid is *Camelus dromedarius*.

4. The composition of claim 1, wherein said pathogen is intact or any fraction treated with heat, formalin or cell lysate.

5. The composition, of claim 1, wherein said immunized Camelid milk is, treated at a temperature of 0° C. for 1-2 hours and centrifuged at 15000 rpm for the removal of lipids.

6. The composition of claim 1, wherein said enzyme is rennin, and said chemical is acetic acid.

7. A process for preparing the composition of claim 1, comprising;
    Immunizing a female camelid with a vaccine of *Escherichia coli* (*E. coli*), *Helicobacter Pylori* (*H. Pylori*) or *Campylobacter jejuni* (*C. jejuni*);
    Obtaining milk from the immunized camelid;
    Treating said milk at a temperature of 0° C. for 1-2 hours and centrifuging at 15000 rpm to remove lipids;
    Treating said milk with rennin or acetic acid to reduce protein content;
    Pasteurizing said milk at a temperature ranging from 65° C. 72° C. for 15 minutes; and
    Adding an acceptable carrier to the pasteurized milk.

8. The process of claim 7, wherein said camelid is from the genus *Camelus, Llama*, or *Vicuna*.

9. The process of claim 8, wherein said camelid is *Camelus dromedarius*.

10. A method for the treatment of a gastrointestinal infection caused by *E. coli, H. pylori*, and/or *C. jejuni* in an infected human comprising administering an effective amount of the composition of claim 1 to the infected human.

* * * * *